United States Patent [19]

Berger

[11] Patent Number: 5,372,145
[45] Date of Patent: Dec. 13, 1994

[54] SURGICAL HAND SUPPORT APPARATUS

[76] Inventor: J. Lee Berger, 895 Mohawk Rd., Franklin Lakes, N.J. 07417

[21] Appl. No.: 945,383
[22] Filed: Sep. 16, 1992
[51] Int. Cl.⁵ .......................... A61F 5/37; A61F 5/00
[52] U.S. Cl. ..................................... 128/878; 602/20; 602/21
[58] Field of Search ...................... 128/877, 878, 879; 602/20, 21, 22, 5, 9, 13

[56] References Cited

U.S. PATENT DOCUMENTS

| | | | |
|---|---|---|---|
| 2,266,230 | 12/1941 | Mazzeo et al. | 128/133 |
| 2,537,323 | 9/1944 | Goldberg | 602/21 |
| 3,476,108 | 11/1969 | Matukas | 128/133 |
| 3,762,401 | 10/1973 | Tupper | 128/879 |
| 3,901,227 | 8/1975 | Klatskin | 128/877 |
| 4,370,976 | 2/1983 | Wanchik | 602/22 |
| 4,453,933 | 6/1984 | Speaker | 128/877 |
| 4,672,955 | 6/1987 | Cooper | 602/5 |
| 4,909,264 | 3/1990 | Wadsworth, III et al. | 128/845 |
| 4,941,480 | 7/1990 | McLean et al. | 128/878 |
| 4,982,744 | 1/1991 | Stanec | 128/877 |
| 5,025,801 | 6/1991 | Callaway | 128/877 |
| 5,136,743 | 8/1992 | Pirela-Cruz | 128/878 |
| 5,140,998 | 8/1992 | Vickers | 128/878 |

Primary Examiner—Michael A. Brown

[57] ABSTRACT

A surgical hand support apparatus having a base block with a finger securing assembly that includes two uprights, a center post positioned between the uprights, a cross member interconnecting the uprights and positioned around the center post and a locking mechanism mounted on the center post to lock the cross member against the fingers of the patient. A thumb securing assembly is also mounted to the base block, the thumb securing assembly includes a standard support member secured to the base block and a hook shaped rod rotatably mounted in the standard support member, the standard support member defining a slot through which a post extending from the side of the base block extends allowing the standard support member and associated hook shaped rod to be reciprocated for selective positioning around the thumb of the patient. A wrist securing assembly, is incorporated having a plurality of brackets slidably mounted to the base block and a cylindrical cross bar mounted in the uprights. A lock screw is connected to the cylindrical cross bar to lock the cross bar in place to secure the wrist of the patient and allow selective positioning of surgical instruments with respect to the hand.

19 Claims, 4 Drawing Sheets

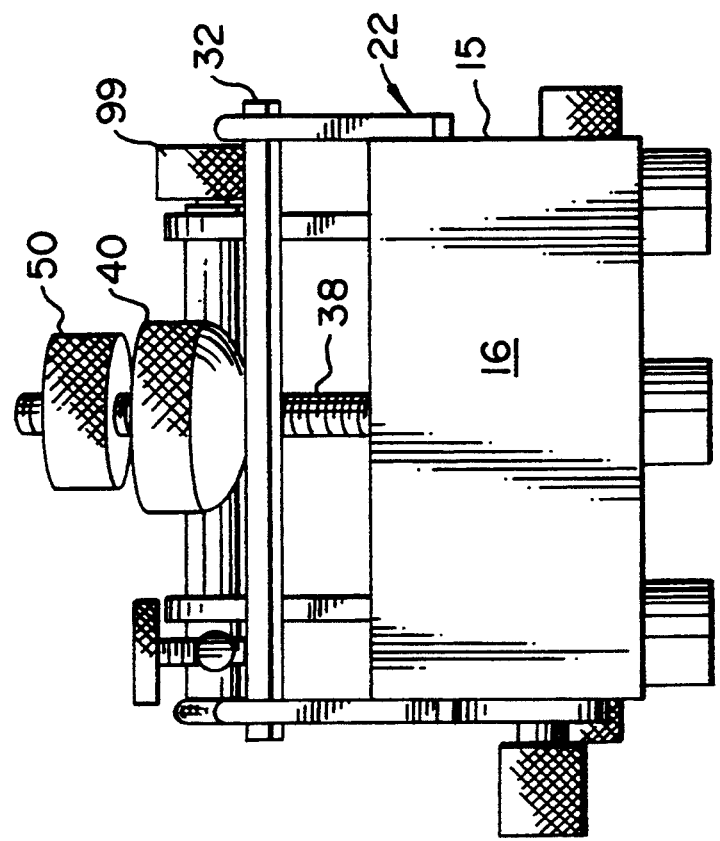
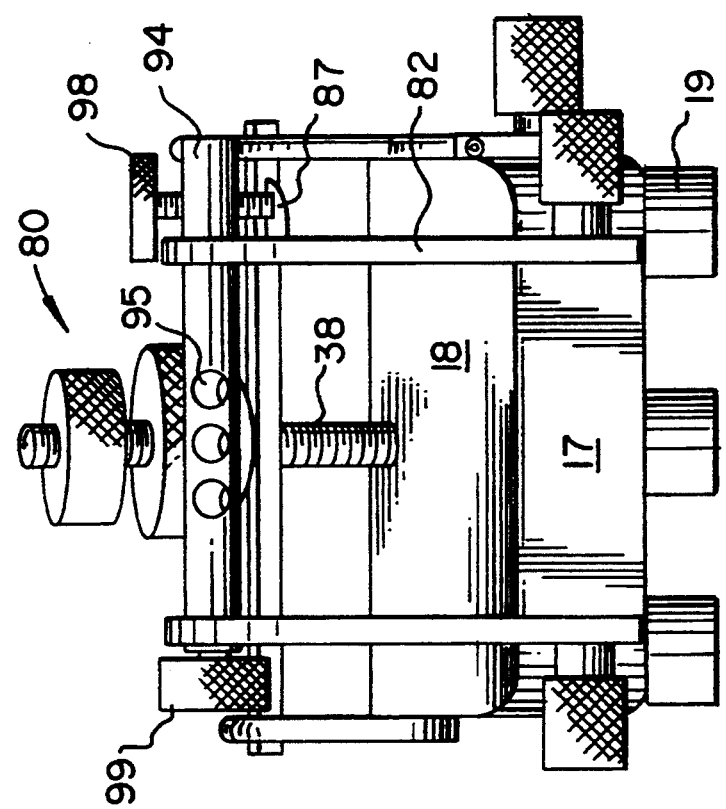
FIG. 4
FIG. 3

SURGICAL HAND SUPPORT APPARATUS

BACKGROUND OF THE INVENTION

The present invention is directed towards a device for immobilizing a patient's hand while holding the hand to a support board in order to facilitate various surgical procedures including endoscopy carpal tunnel release, percutaneous carpal tunnel-plasty and arthoscopy of the hand and wrist.

The human hand is the site of a large number of operative procedures and prior art hand restraints have not been able to fully immobilize the hand during a number of surgical procedures.

A number of restraint devices have been used to support and restrain a patient's hand for intravenous administration and various surgical procedures. U.S. Pat. No. 4,982,744 discloses an immobilizing apparatus including a composite sheet and arm board. The composite sheet includes an adhesive surface on one side and loop fastener on the other side. The arm board includes a fabric hook fastener which engages and holds the hook fasteners of the composite sheet. The patient's hand and/or forearm is secured to the composite sheet by placing the hand and/or forearm on the adhesive surface, the hooked surface of the composite sheet having been previously mounted to the hooked surface of the arm board. A hand belt constructed of fabric loop fasteners, can be used with the restraining device to immobilized the hand.

U.S. Pat. No. 4,941,480 discloses a splint for immobilizing an patient's arm consisting of a three sided plastic foam support which is secured to the patient's arm with a series of Velcro ® straps.

U.S. Pat. No. 5,025,801; 4,909,264; 3,762,401; and 2,266,230, each disclose devices which temporarily restrain or support the hand and/or forearm using straps or bands to secure the hand for surgery or intravenous therapy. The use of straps is disadvantageous in that the straps are difficult to secure and also limit accessibility of the patient's hand and/or forearm.

SUMMARY OF THE INVENTION

In the present invention, the patient's hand is placed on an inclined plastic support base with the fingers, thumb and wrist being separately adjustably secured to the support base by rigid assemblies. The wrist assembly is also provided with a cross bar allowing instrumentation to be inserted therein for use in operating on the hand.

Thus, the present inventive device supports the hand and wrist comfortably for surgical procedures, maximizing the stability which decreases the fatigue of the surgeon's hands during delicate hand surgery. An assistant is not necessary because the inventive device secures the wrist, hand and fingers and is anatomically contoured for hand surgery with adjustable finger and thumb supports.

It is an object of the invention to provide a custom designed device for conventional hand surgery, endoscopic carpal tunnel release, percutaneous carpal tunnel plasty and arthoscopy of the hand and wrist.

It is a further object of the invention to provide for a stop guide which can be utilized to position endoscope or groove guides protecting underlined structures while supporting the hand and wrist during surgical procedures including arthroscopy, carpal tunnel release, open reduction or fixation of fractures. The device is also radiolucent facilitating interoperative radiograms for image intensification without moving the hand or wrist during surgery.

It is also an additional object of the invention to provide a device which is reusable, can be autoclaved, and is long lasting allowing the general handing of delicate tissues required of hand surgery.

In the accompanying drawings, there is shown an illustrative embodiment of the invention from which these and other of objectives, novel features and advantages will be readily apparent.

BRIEF DESCRIPTION OF THE DRAWINGS

FIG. 3 is a rear elevational view of the surgical hand support apparatus shown in FIG. 1;

FIG. 4 is a front elevational view of the surgical hand support apparatus shown in FIG. 1;

DETAILED DESCRIPTION OF THE INVENTION

Figure 1:
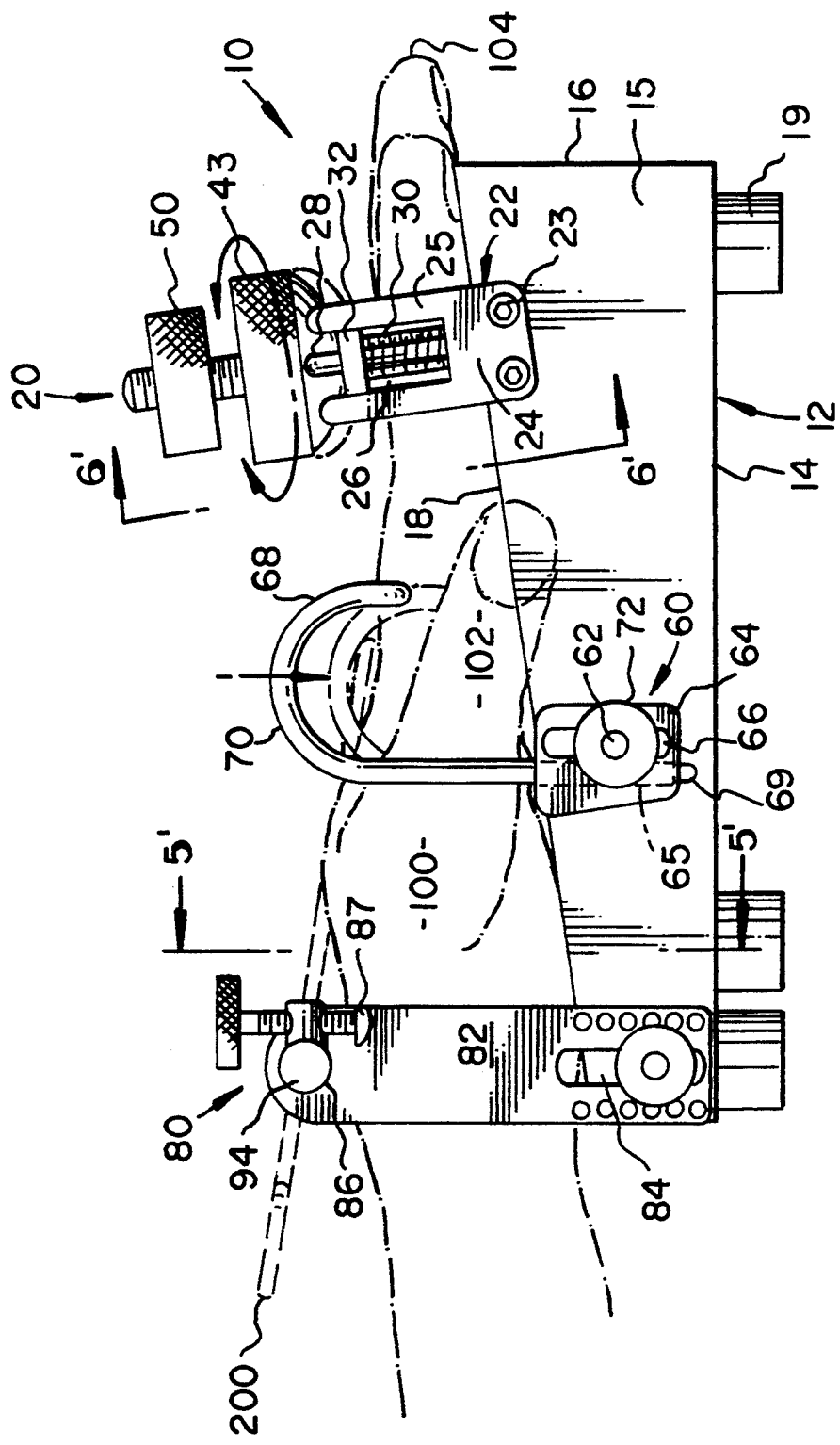
FIG. 1 is side elevational view of the surgical hand support apparatus with an inserted patient's hand shown in phantom.
Figure 2:
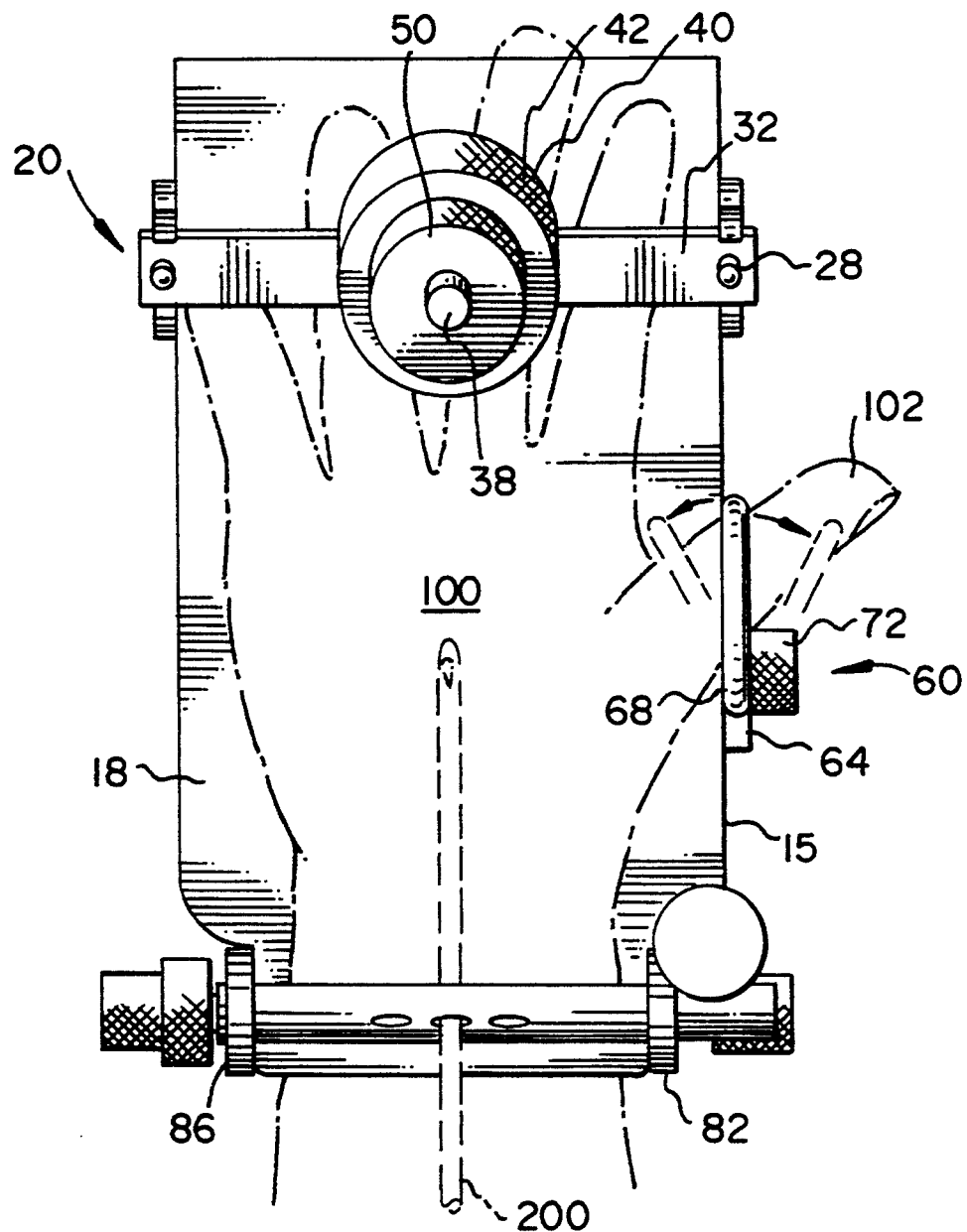
FIG. 2 is a top plan view of the surgical hand support apparatus shown in FIG. 1 with an inserted patient's hand shown in phantom.

The preferred embodiment and best mode of the invention is shown in FIGS. 1-6 and is shown by the figures. The surgical hand support apparatus 10 is designed to hold a hand 100, thumb 102 and fingers 104 in a fixed position for surgery and image intensification.

The surgical hand support apparatus 10 is constructed with an inclined plastic base block 12 constructed of a radiolucent plastic material which can be autoclaved having a planar base surface 14 with perpendicular side surfaces 15, front surface 16, rear surface 17 and an inclined hand support surface 18. The planar base surface 14 is provided with a plurality of support feet 19 which keep the block from slipping on the surface on which it is seated. The feet 19 are constructed of a material having a high coefficient of friction such as rubber or plastic to keep the block from slipping.

Figure 5:
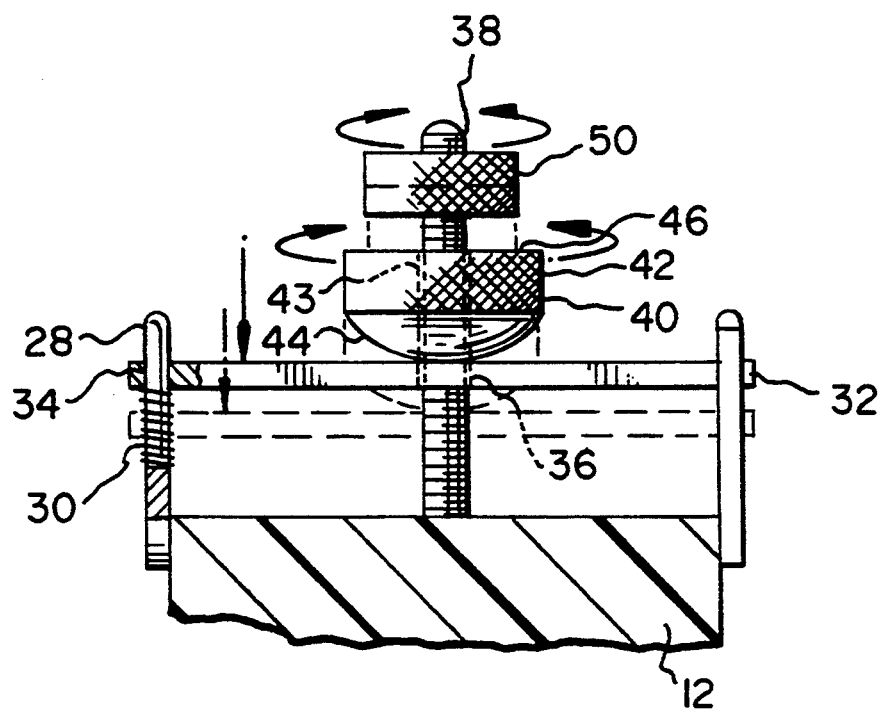
FIG. 5 is a cross sectional view of the surgical hand support apparatus taken along lines 5'—5' on FIG. 1.

The surgical hand support apparatus 10 is provided with a finger securing assembly 20 as shown in FIGS. 1, 2, 4 and 5 which incorporates a pair of stainless steel upright side yokes 22 which are secured to the base block 12 by screws 23. The side yokes 22 have a yoke base 24 with yoke arms 25. The yoke arms 25 define a U-shaped finger bar channel 26 which receives the finger support bar 32. A finger bar support pin 28 is mounted to the yoke base 24 and extends upward between yoke arms 25. Finger support bar springs 30 are mounted around the finger bar support pins 28 and are seated on yoke base 24. The springs 30 engage and outwardly bias a finger support bar 32 which is mounted on the finger support pins 28. The finger support bar 32 is rectangular with a flat polished planar surface and like the yokes 22 it is constructed of stainless steel. The finger support bar 32 is provided with support pin apertures 34 at each end having a diameter which allows the finger support bar 32 to be mounted on the finger bar support pins 28 and easily slide up and down in channel 26 against the biassing forces of bar springs 30 or the downward torque force of threaded positioning knob 40. The positioning knob 40 is threaded on a threaded center support post 38 which is secured in the base block 12. The center support post 38 extends through a center post aperture 36 which is centrally positioned in finger support bar 32. The post aperture 36 has a diameter slightly greater than the support post 38 diameter. The positioning knob 40 has a body with a cylindrical knurled outer surface 42, a rounded engaging end 44 which engages finger support bar 32, a through threaded bore 43 which receives the threaded center support post 38, and a flat planar top surface 46 which adapted to receive a threaded knurled locking nut 50. The relationship of the locking knob 40, finger support bar 32 and side yokes 22 is best shown in FIG. 5.

A thumb lock assembly 60 is secured to side 15 of base block 12 to hold thumb 102 in place during surgery. The thumb lock assembly 60 is constructed of a threaded side post 62 secured to the side 15 of base block 12. The side post 62 is preferably screwed into a threaded insert in the plastic base block 12 to hold it in a fixed position or can be unscrewed and removed for storage with the rest of the parts of the thumb assembly if so desired. A slidable support member 64 is provided with a slot 66 which allows the side post 62 to be inserted therein allowing support member 64 to be selectively positioned by sliding it via slot 66 along side post 62. The slidable support member 64 also defines a throughgoing bore 65 which holds a curved thumb containment hook 68. The thumb containment hook 68 is formed with the straight end 69 allowing the containment hook to be inserted in the throughgoing bore 65 with the other end of the thumb support hook being bent or curved at 70 which allows the curved end to be rotated over and around thumb 102. A knurled locking knob or nut 72 is threaded on the side post 62 to secure the slidable support member 64 causing the same to be held in a fixed position after the desired vertical placement of the curved thumb containment hook with relation to the thumb 102 is obtained.

Figure 6:
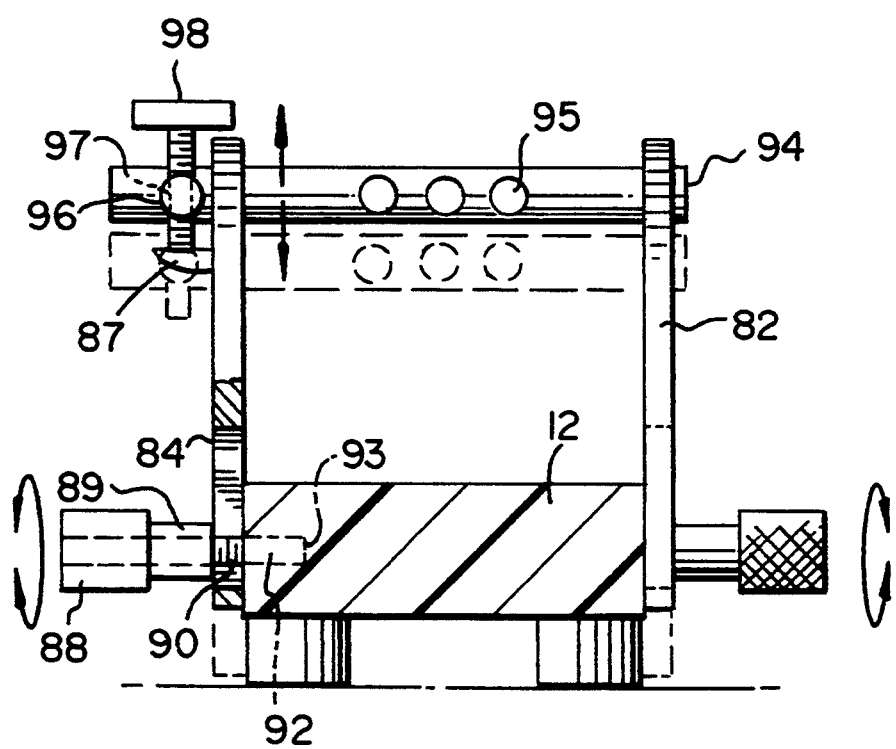
FIG. 6 is a cross sectional view of the surgical hand support apparatus taken along lines 6'—6' on FIG. 1.

A wrist holding assembly 80 as shown in FIGS. 1, 3 and 6 is secured to the base block 12. The wrist holding assembly is constructed with two upright brackets 82 mounted on each side of the base block, each bracket defining an adjustment slot 84 and a cross member aperture 86. One of the bracket uprights is provided with an integral locking seat 87. As shown in FIG. 6, a locking knob 88 with a shaft 89 having an extending screw projection 90 is mounted in a threaded insert 92 in the side 15 of base block 12. The screw projection 90 is threaded into blind bore 93 in the base block with the screw projection 90 extending through the adjustment slot 84, the stepped end of shaft 89 being slightly removed from the outer surface of the upright bracket 82 defining slot 84. The locking knob 88 is rotated, screwing the screw projection 90 into insert 92 so that stepped end of shaft 89 abuts against the upright bracket 82, locking it into the desired vertical position against the base block 12. A cylindrical tool holder and wrist restrainer bar 94 is mounted through the apertures 86 in the upright brackets 82 and supported by the two upright brackets 82. The holder and wrist restrainer bar 94 defines a plurality of throughgoing bores 95 having a diameter sufficient to hold a catheter director or guide 200, which is shown in phantom in FIGS. 1 and 2, in the desired position for the surgery. The holder and wrist restrainer bar 94 also is provided with a locking screw support nipple 96 having a threaded throughgoing bore 97 in which a locking screw 98 is threaded. The locking screw 98 is aligned so that it is adjacent the throughgoing aperture in locking seat 87 and is screwed into the locking seat 87 keeping the bar 94 from rotating. The holder bar 94 has a threaded knurled limit end knob 99 which keeps the holder bar from being pulled or slid out of the upright bracket 82.

When the devices is being used in an operation, the patient's hand 100 is laid on the inclined surface of block 12 with the fingers placed on the upper part of inclined surface 16 and the wrist on the lower part of the inclined surface 16. The finger support bar 32 is then placed over the pins 28 against the springs 30 until the bar 32 engages fingers 104. Tensioning knob 40 is threaded onto center post 38 and rotated downward until the rounded end 44 of knob 40 engages the upper surface of finger support bar 32. Alternatively, knob 40 is rotated downward on the center post 38, driving the bar 32 downward against the expansion of coil springs 30 until the fingers are snugly held between the lower planar surface of support bar 32 and the top inclined surface 16 of block 12. Locking nut 50 is then screwed onto center post 38 against the positioning knob 40 to hold the positioning knob 40 in a locked position. The thumb assembly 60 is then engaged with the patient's thumb 102 by sliding the hook member 68 and its associated support member 64 upward, rotating the hook member 68 over the thumb and sliding support member 64 downward until the bottom of hook 68 engages the thumb 102 holding it against the surface 16 of block 12. The locking knob 72 is then rotated to hold the support member and thumb hook in a fixed position. The wrist restraining bar 94 is then inserted through bores 86 in the bracket uprights 82 and the limit knob 99 is screwed into the end of the wrist restraining bar. The locking knobs 88 are loosened and the wrist holding assembly 80 is slid along slots 84 of the bracket uprights 82 until the wrist restraining bar 94 engages the bottom of the wrist. The bracket uprights 82 are then locked into position by screwing projection 90 into insert 92 so that the stepped end of locking shaft 89 abuts against the external surface of bracket upright 82 holding it in a fixed position against block 12. Locking screw 98 is screwed into locking seat 87 holding the restraining bar 94 in fixed position for insertion of surgical instruments. Necessary surgical instruments such as guides 200 can be inserted through bores 95 against the hand 102 at which time surgery commences.

In the foregoing description, the invention has been described with reference to a particular preferred embodiment, although it is to be understood that specific details shown are merely illustrative, and the invention may be carried out in other ways without departing from the true spirit and scope of the following claims:

What is claimed is:

1. A surgical hand support apparatus comprising a base block adapted to support a patient's hand, a rigid finger securing means mounted to said base block, a thumb securing means mounted to said base block, said thumb securing means comprising a support member moveably mounted to said base block and a hook shaped rod moveably mounted to said support member, and fastening means allowing said support member to be moveably positioned with respect to said base block, and a rigid wrist securing assembly mounted to said base block.

2. An apparatus as claimed in claim 1 wherein said base block has an inclined upper surface and is constructed of plastic.

3. An apparatus as claimed in claim 2 wherein said plastic is radiolucent.

4. An apparatus as claimed in claim 1 wherein said finger securing means comprises a plurality of uprights mounted to said base block, a center post mounted to said base block and positioned between said uprights, a cross member slidably mounted on said uprights and positioned around said center post and locking means mounted on said center post to hold said cross member in a predetermined position.

5. An apparatus as claimed in claim 4 including pin means extending from each upright, said pin means having spring means mounted thereon which support said cross member and constantly urge said cross member away from the base block.

6. An apparatus as claimed in claim 4 wherein said cross member defines a center aperture which receives said center post allowing said cross member to move along said center post and an aperture on each end which receives pin means mounted on each upright.

7. An apparatus as claimed in claim 1 including removable side post means mounted to said base block, said support member defining a slot, said side post means extending through said slot allowing said support member to be slidably moved with respect to said side post means.

8. An apparatus as claimed in claim 1 wherein said base block has a plurality of feet extending from said base block, said feet being provided with a friction surface to keep said base block in place.

9. An apparatus as claimed in claim 1 wherein said wrist assembly comprises a plurality of bracket members, a cross bar mounted in said bracket members and locking means connected to said cross bar to lock said cross bar in place.

10. An apparatus as claimed in claim 9 wherein said cross bar defines a plurality of apertures therein allowing surgical instruments to be placed therein and held in a predetermined orientation and each bracket member defines slot means allowing said bracket member to be moved vertically with regard to a lower planar surface of said block.

11. An apparatus as claimed in claim 10 wherein at least one of said bracket members is provided with a locking seat and said cross bar has a projecting nipple holding lock means to hold said cross bar in a specific position.

12. An apparatus as claimed in claim 9 wherein said cross bar is cylindrical and is provided with stop means on at least one end to limit movement of said cylindrical cross bar in said bracket members.

13. A surgical hand support apparatus comprising a base block, a finger securing means mounted to said base block, said finger securing means comprising a plurality of uprights mounted to said base block, a center post mounted to said base block positioned between said uprights, a cross member positioned between said uprights and positioned around said center post and locking means mounted on said center post to lock said cross member against a patient's fingers inserted onto said base block, a thumb securing means mounted to said base block, said thumb securing means comprising a standard secured to said block and a curved rod member secured to said standard member, said curved rod member being rotatable in said standard member and fastening means allowing said standard member to be moved with respect to said base block and fastened in a fixed position, and a wrist securing means mounted to said base block, said wrist securing means comprising a plurality of bracket members, a cross bar mounted in said bracket member and locking means mounted on said cross bar to lock said cross bar in a predetermined position.

14. An apparatus as claimed in claim 13 wherein said base block is plastic with an inclined upper surface and a planar lower surface.

15. An apparatus as claimed in claim 13 wherein said plastic is radiolucent.

16. An apparatus as claimed in claim 13 wherein said base block has a plurality of feet extending from said base block, said feet being provided with a friction surface to keep said base block in place once it has been set down on a surface.

17. An apparatus as claimed in claim 13 wherein said wrist securing means bracket member defines a cross bar aperture and a slot, and includes bracket member lock means comprising a stepped shaft, a threaded end projection extending from one end of said shaft having a diameter less then the width of the bracket member slot and a knurled head secured to the other end of said shaft.

18. A surgical hand support apparatus comprising a base block with a finger securing assembly mounted thereto, said finger securing assembly comprising yoke members placed on opposite sides of said base block, a center post mounted to said base block positioned between yoke members, a cross member moveably mounted on pin means on said yoke members, spring means mounted on said pin means engaging said cross member to place a force on said cross member, and a locking mechanism mounted on said center post to hold the cross member against the force of the spring means in an predetermined position, a thumb securing assembly mounted to the base block, the thumb securing assembly comprises a standard support member secured to the base block and a hook shaped rod rotatably mounted in the standard support member, the standard support member defines a slot through which a post extending from the side of the base block extends allowing the standard support member and associated hook shaped rod to be reciprocated for selective positioning of the hook shaped rod around the thumb of a patient, a wrist securing assembly comprising a plurality of uprights, a cylindrical cross bar mounted in the uprights and a lock screw connected to the cylindrical cross bar to lock the cylindrical cross bar in place to secure the wrist of the patient and allow selective positioning of surgical instruments with respect to the hand.

19. A surgical hand support apparatus comprising a base block with an inclined upper surface adapted to support a patient's hand, a finger securing means mounted to said base block, and a rigid wrist securing assembly mounted to said base block, said wrist securing assembly comprising a plurality of support members, a cross bar mounted on said support members and locking means connected to said cross bar to lock said cross bar in a fixed position, said cross bar defining a plurality of apertures therein allowing surgical instruments to be placed therein and held in a predetermined orientation, each support member defining positioning means allowing said support member to be moved toward and away from the upper surface of said block.

* * * * *